United States Patent
Hong et al.

(10) Patent No.: US 11,276,490 B2
(45) Date of Patent: Mar. 15, 2022

(54) METHOD AND APPARATUS FOR CLASSIFICATION OF LESION BASED ON LEARNING DATA APPLYING ONE OR MORE AUGMENTATION METHODS IN LESION INFORMATION AUGMENTED PATCH OF MEDICAL IMAGE

(71) Applicants: SEOUL WOMEN'S UNIVERSITY INDUSTRY-UNIVERSITY COOPERATION FOUNDATION, Seoul (KR); INDUSTRY-ACADEMIC COOPERATION FOUNDATION, YONSEI UNIVERSITY, Seoul (KR)

(72) Inventors: Helen Kim Hong, Seoul (KR); Hansang Lee, Seoul (KR); Joon Seok Lim, Seoul (KR)

(73) Assignees: SEOUL WOMEN'S UNIVERSITY INDUSTRY-UNIVERSITY COOPERATION FOUNDATION, Seoul (KR); INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 43 days.

(21) Appl. No.: 16/849,779

(22) Filed: Apr. 15, 2020

(65) Prior Publication Data
US 2020/0335197 A1    Oct. 22, 2020

(30) Foreign Application Priority Data
Apr. 16, 2019    (KR) .................... 10-2019-0044264

(51) Int. Cl.
| | | |
|---|---|---|
| G06K 9/00 | (2006.01) | |
| G16H 30/20 | (2018.01) | |
| G06K 9/62 | (2022.01) | |
| G06T 7/00 | (2017.01) | |
| G06N 3/08 | (2006.01) | |

(52) U.S. Cl.
CPC .......... G16H 30/20 (2018.01); G06K 9/6267 (2013.01); G06N 3/08 (2013.01); G06T 7/0012 (2013.01)

(58) Field of Classification Search
CPC .... B60Q 1/18; B60Q 5/00; E01H 5/04; E01H 5/061; E01H 5/065; E01H 5/066; G06K 2209/05; G06K 9/6256; G06K 9/6267; G06N 3/0454; G06N 3/0472; G06N 3/08; G06T 2207/10081; G06T 2207/10088; G06T 2207/10104; G06T 2207/10116; G06T 2207/20081; G06T 2207/20084; G06T 2207/30096; G06T 7/0012; G16H 30/20; G16H 30/40; G16H 50/20
See application file for complete search history.

(56) References Cited

U.S. PATENT DOCUMENTS

| | | | | |
|---|---|---|---|---|
| 2014/0036054 A1* | 2/2014 | Zouridakis | ........... | A61B 5/0077 348/77 |
| 2016/0364878 A1* | 12/2016 | Guo | ......................... | G06T 7/11 |
| 2019/0171908 A1* | 6/2019 | Salavon | ............... | G06N 3/0481 |

* cited by examiner

*Primary Examiner* — Xin Jia
(74) *Attorney, Agent, or Firm* — Studebaker & Brackett PC

(57) ABSTRACT

A learning-based lesion classification method performed by a computer is provided. The method includes obtaining a medical image including lesion regions, extracting at least one sample region from the lesion regions within the medical image, generating LINA patch data based on the at least one sample region, and classifying the lesion regions within the medical image by performing learning based on the LINA patch data.

10 Claims, 5 Drawing Sheets

METHOD AND APPARATUS FOR CLASSIFICATION OF LESION BASED ON LEARNING DATA APPLYING ONE OR MORE AUGMENTATION METHODS IN LESION INFORMATION AUGMENTED PATCH OF MEDICAL IMAGE

CROSS-REFERENCE TO RELATED APPLICATIONS

A claim for priority under 35 U.S.C. § 119 is made to Korean Patent Application No. 10-2019-0044264 filed Apr. 16, 2019 in the Korean Intellectual Property Office, the entire contents of which are hereby incorporated by reference.

BACKGROUND

Embodiments of the inventive concept described herein relate to a learning data-based lesion classification method and apparatus that generates lesion information augmented patch (LINA patch) including information about internal and boundary regions of a lesion and uses the data generated through general data augmentation and generative adversarial Network (GAN)-based data augmentation method.

Nowadays, deep learning is being widely used to analyze medical images. The deep learning is defined as a set of machine learning algorithms that attempt a high level of abstraction (i.e., the task of summarizing the core contents or functions in a large amount of data or complex data) through the combination of several nonlinear transformation methods. The deep learning may be roughly classified as a field of machine learning that teaches a person's mindset to computers.

When the learning is performed using such the deep learning, machine learning, or the like, there is a need for a large amount of learning data. However, because surgical images are obtained during actual surgical procedures, the amount of data is small and it is difficult to obtain various types of surgical images.

Besides, because sizes of lesions included in the medical image are small and the lesions have similar characteristics to one another, it is not easy to extract lesions from the medical images. Furthermore, even though lesions are extracted from the medical images, it is frequently difficult to distinguish between the types of lesions.

Accordingly, there is a need for the technology for constructing a data set necessary to perform deep learning, machine learning, or the like using medical images and classifying lesions by effectively extracting the lesions from medical images.

SUMMARY

Embodiments of the inventive concept provide a learning-based lesion classification method and apparatus.

Embodiments of the inventive concept provide a method and an apparatus that classify lesions in images using deep learning-based learning.

Embodiments of the inventive concept provide a method and an apparatus that generate LINA patch including information about internal and boundary regions of a lesion, using general data augmentation and GAN-based data augmentation.

Embodiments of the inventive concept provide a method and an apparatus that generate patch data augmenting lesion information in an image including microscopic lesions.

Embodiments of the inventive concept provide a method and an apparatus that provide LINA patch data through GAN learning.

The technical problems to be solved by the present inventive concept are not limited to the aforementioned problems, and any other technical problems not mentioned herein will be clearly understood from the following description by those skilled in the art to which the inventive concept pertains.

According to an exemplary embodiment, a learning-based lesion classification method performed by a computer includes obtaining a medical image including a lesion region, extracting at least one sample region from the lesion region within the medical image, generating lesion information augmented patch (LINA patch) data based on the at least one sample region, and classifying lesions included in the lesion region within the medical image by performing learning based on the LINA patch data.

In an exemplary embodiment, the extracting of the at least one sample region may include selecting at least one arbitrary point from the lesion region within the medical image and extracting the respective at least one sample region with a center at the respective at least one arbitrary point.

In an exemplary embodiment, the generating of the LINA patch data may include generating the LINA patch data by positioning the at least one sample region in an 'N×N'-sized patch.

In an exemplary embodiment, the method may further include augmenting lesion information about the lesion region within the medical image. The generating of the LINA patch data may include positioning the at least one sample region extracted from the medical image including the augmented lesion information in the 'N×N'-sized patch. The augmenting of the lesion information about the lesion region may include performing at least one of scaling and rotation on the lesion region within the medical image.

In an exemplary embodiment, the generating of the LINA patch data may include learning the LINA patch data, using generative adversarial network (GAN) and generating synthetic data for the LINA patch data, through the learning using the GAN.

In an exemplary embodiment, the classifying of the lesions included in the lesion region within the medical image may include performing the learning using Convolutional Neural Network (CNN) based on at least one of the LINA patch data and the synthetic data and classifying the lesions included in the lesion region through the learning using the CNN.

In an exemplary embodiment, the performing of the learning using CNN may include performing the learning based on at least one of texture information of a lesion and boundary information of a lesion, which are included in the lesion region.

In an exemplary embodiment, the sample region may be a region formed of a square of a predetermined size, and a size of the sample region may be determined depending on a size or shape of the lesion region. The LINA patch data may include 'N×N' sample regions formed of the square of the predetermined size.

According to an exemplary embodiment, an apparatus may include a memory storing one or more instructions and a processor executing the one or more instructions stored in the memory. The one or more instructions, when executed by the processor, cause the processor to obtain a medical image including a lesion region, to extract at least one sample region from the lesion region within the medical image, to generate LINA patch data based on the at least one sample region, and to classify lesions included in the lesion region within the medical image by performing learning based on the LINA patch data.

According to an exemplary embodiment, a computer program may be stored in a computer-readable recording medium to perform the learning-based lesion classification method, in combination with a computer being hardware.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
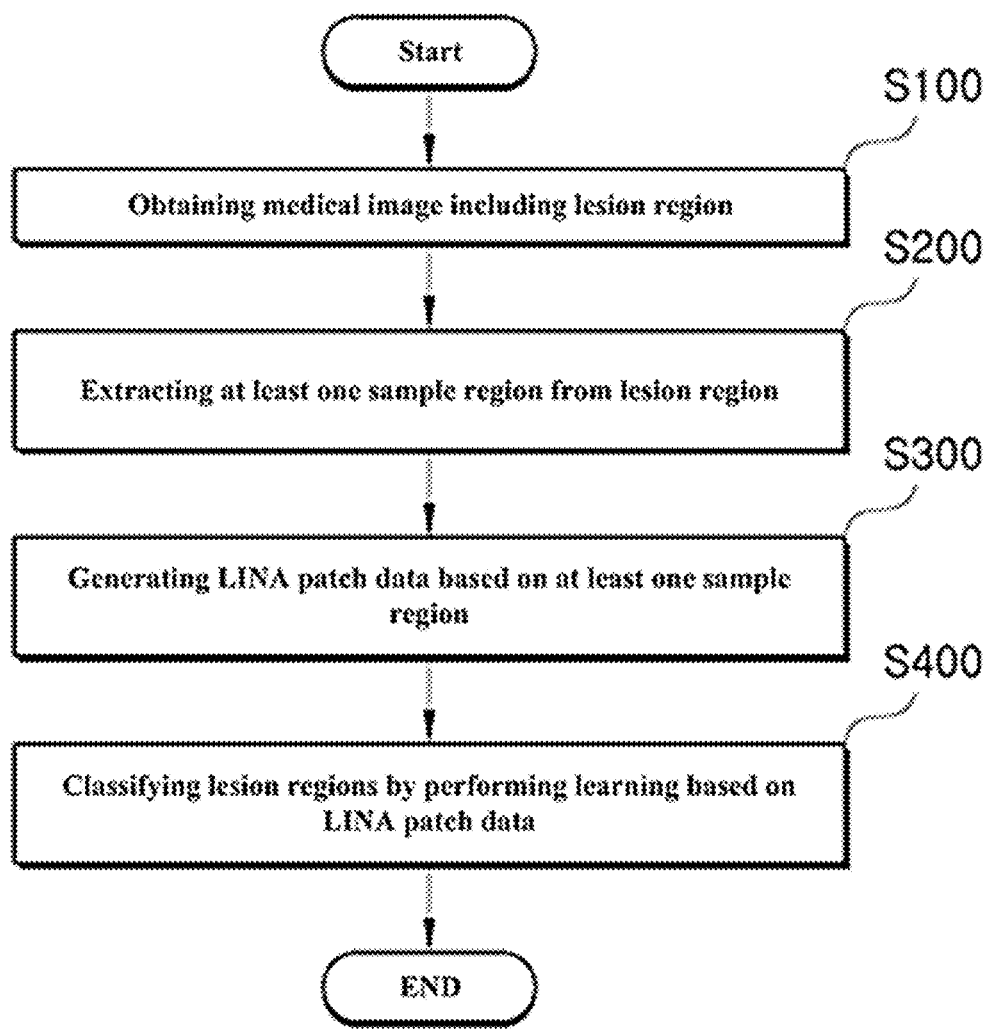
FIG. 1 is a flowchart schematically illustrating a learning-based lesion classification method according to an embodiment of the inventive concept.

Advantage points and features of the inventive concept and a method of accomplishing thereof will become apparent from the following description with reference to the following figures, wherein embodiments will be described in detail with reference to the accompanying drawings. The inventive concept, however, may be embodied in various different forms, and should not be construed as being limited only to the illustrated embodiments. Rather, these embodiments are provided as examples so that the inventive concept will be thorough and complete, and will fully convey the concept of the inventive concept to those skilled in the art. The inventive concept may be defined by scope of the claims. Meanwhile, the terminology used herein to describe embodiments of the inventive concept is not intended to limit the scope of the inventive concept.

The terminology used herein is for the purpose of describing embodiments and is not intended to limit the inventive concept. In the specification, the singular forms include plural forms unless particularly mentioned. The terms "comprises" and/or "comprising" used herein does not exclude presence or addition of one or more other elements, in addition to the aforementioned elements. The same reference numerals denote the same elements throughout the specification. As used herein, the term "and/or" includes any and all combinations of one or more of the associated components. It will be understood that, although the terms "first", "second", etc., may be used herein to describe various components, these components should not be limited by these terms. These terms are only used to distinguish one component from another component. Thus, a first component discussed below could be termed a second component without departing from the teachings of the inventive concept.

Unless otherwise defined, all terms (including technical and scientific terms) used herein have the same meaning as commonly understood by those skilled in the art to which the inventive concept pertains. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein.

The term "unit" or "module" used herein may refer to software or hardware such as field programmable gate array (FPGA) or application specific integrated circuit (ASIC), and the "unit" or "module" may perform some functions. However, the "unit" or "module" may be not limited to software or hardware. The "unit" or "module" may be configured to exist in an addressable storage medium or may be configured to reproduce one or more processors. Therefore, as an example, "units" or "module" may include various elements such as software elements, object-oriented software elements, class elements, and task elements, processes, functions, attributes, procedures, subroutines, program code segments, drivers, firmware, microcodes, circuits, data, databases, data structures, tables, arrays, and variables. Functions provided in "units" or modules and elements may be combined into a smaller number of "units" or modules and elements or may be divided into additional "units" or modules and elements.

In this specification, a 'computer' includes all various devices capable of providing results to a user by performing arithmetic processing. For example, the computer may correspond to not only a desktop personal computer (PC) or a notebook but also a smart phone, a tablet PC, a cellular phone, a personal communication service phone (PCS phone), a mobile terminal of a synchronous/asynchronous International Mobile Telecommunication-2000 (IMT-2000), a palm PC, a personal digital assistant (PDA), and the like. Besides, when the head mounted display (HMD) device includes a computing function, the HMD device may be a computer. Furthermore, the computer may correspond to a server that receives a request from a client and processes information.

Hereinafter, embodiments of the inventive concept will be described in detail with reference to accompanying drawings.

FIG. 1 is a flowchart schematically illustrating a learning-based lesion classification method according to an embodiment of the inventive concept.

For convenience of description, the method of FIG. 1 is described as being performed by a computer; however, the subject of each operation is not limited to a specific apparatus; the method of FIG. 1 may be used as the meaning including an apparatus capable of performing computing processing. That is, in an embodiment, the computer may refer to an apparatus capable of performing a learning-based lesion classification method according to an embodiment of the inventive concept.

Referring to FIG. 1, a learning-based lesion classification method according to an embodiment of the inventive concept may include operation S100 of obtaining a medical image including lesion regions, operation S200 of extracting at least one sample region from the lesion region within the medical image, operation S300 of generating LINA patch data based on the at least one sample region, and operation S400 of classifying the lesion regions within the medical image by performing learning based on the LINA patch data. Hereinafter, the detailed description of each operation is provided.

In S100, the computer may obtain a medical image including a lesion region.

Herein, the medical image may be an image captured by a medical imaging device; the medical image may include the entire medical image data obtained using, for example, CT, PET, MRI, X-Ray, and the like.

The lesion region refers to a region corresponding to a lesion portion in a specific body part within the medical image obtained by capturing a specific body part of a subject (e.g., a patient) using CT, PET, MRI, X-Ray, or the like. For example, the lesion region may include a liver lesion portion in the medical image obtained by capturing abdomen or may include lesions such as cyst, hemangioma, metastasis, and the like in the medical images obtained by capturing various body parts.

In S200, the computer may extract at least one sample area from the lesion area within the medical image.

In an embodiment, the computer may select at least one arbitrary point from the lesion region within the medical image and may extract at least one sample region with the center at each selected at least one arbitrary point.

At this time, the computer may augment lesion information about the lesion region within the medical image and may extract at least one sample region from the lesion region including the augmented lesion information. In an embodiment, the computer may augment lesion information by performing at least one of scaling and rotation on the lesion region within the medical image.

In S300, the computer may generate LINA patch data based on the at least one sample region.

In an embodiment, the computer may generate the LINA patch data by positioning the at least one sample region in an 'N×N'-sized patch. At this time, the computer may augment lesion information through scaling and/or rotation of the lesion region, may extract at least one sample region based on the augmented lesion information, and may position the at least one sample region in the 'N×N'-sized patch. Here, 'N' may mean an arbitrary positive integer; for example, 'N' may be set to a value of 1 or more. In another embodiment, the LINA patch may have an 'N×M' size as well as an 'N×N' size. Here, 'N' and 'M' are arbitrary positive integers and may have different values from each other.

According to an embodiment, the computer may learn the LINA patch data using GAN and may generate synthetic data similar to the LINA patch data as the learning result. Here, it may be understood that the meaning of "similar" is the meaning of the same as or close to reality. Accordingly, the synthetic data similar to the LINA patch data refers to false data (i.e., synthesized data) close to (not real data) reality and generated by learning the real LINA patch data. The specific process of generating synthetic data using GAN will be described with reference to FIG. 5.

In S400, the computer may classify lesion regions included in the medical image by performing learning based on the LINA patch data.

In an embodiment, the computer may construct the LINA patch data generated based on the sample region extracted from the lesion regions within the medical image as a learning data set. In addition, the computer may construct the LINA patch data including augmented lesion information as the learning data set, by performing scaling or/and rotating on the lesion information. Also, the computer may construct synthetic data generated through GAN as the learning data set. The computer may perform learning based on the learning data set constructed as described above and may classify lesions included in the lesion region as the learning result.

Figure 2:
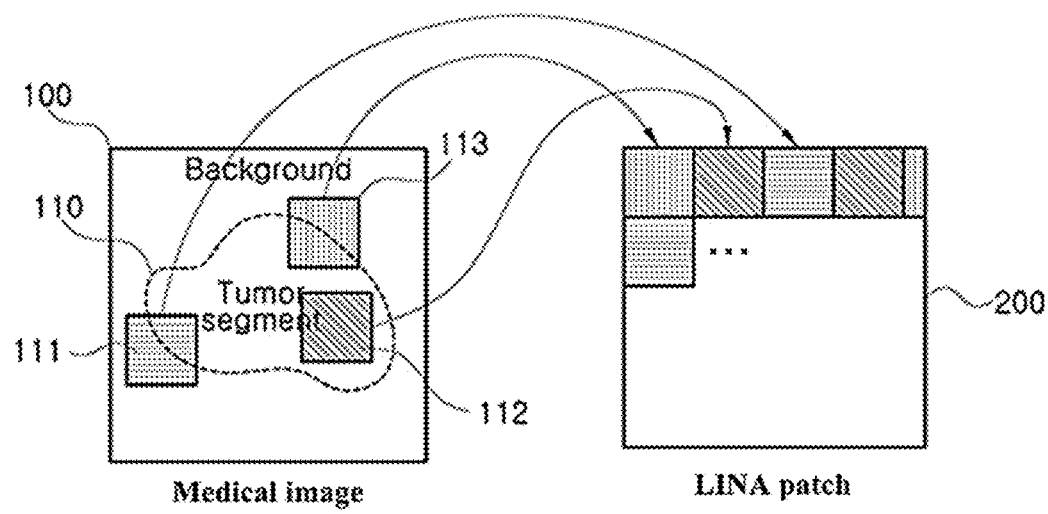
FIG. 2 is a view for describing a process of generating LINA patch data by extracting a sample region from a medical image including a lesion region, according to an embodiment of the inventive concept.

FIG. 2 is a view for describing a process of generating LINA patch data by extracting a sample region from a medical image including a lesion region, according to an embodiment of the inventive concept.

Referring to FIG. 2, first of all, a computer may obtain a medical image 100 including a lesion region 110. Besides, the computer may detect a lesion in the medical image 100, may assign the lesion as Region of Interest (ROI), and may determine the lesion region 110 based on the assigned ROI. That is, the computer may obtain information about the location and size of the lesion region 110 by segmenting the lesion region 110 from the medical image 100.

The computer may extract at least one sample region 111, 112, or 113 with the center at the lesion region 110 within the medical image 100 and may position the extracted sample regions 111, 112, and 113 at an 'N×N'-sized patch 200.

For example, the computer may select an arbitrary point (a first point) in the lesion region 110 and may extract the first sample region 111 based on the selected arbitrary point (the first point). Moreover, the computer may position the extracted first sample region 111 in the 'N×N'-sized patch 200. As such, the computer may repeat a process of extracting the sample regions 111, 112, and 113 from the lesion region 110 and positioning the sample regions 111, 112, and 113 in the 'N×N'-sized patch 200 and may finally fill the 'N×N'-sized patch 200 with sample regions obtained by sampling the lesion regions. That is, the computer may obtain the 'N×N'-sized patch 200 composed of sample regions as LINA patch data.

Herein, the sample region may be a region formed of a square with a predetermined size. The size of the sample region may be determined depending on the shape, size, and feature of the lesion region. For example, when the size of the lesion region is large, the size of the sample region may be set to be large; on the other hand, when the size of the lesion region is small, the size of the sample region may also be set to be small. Alternatively, when the shape of the lesion region is irregular, the size of the sample region may be set to be small; when the shape of the lesion region is regular, the size of the sample region may be set to be large. Alternatively, the size of the sample region may be determined depending on feature information (e.g., pattern information) such as texture features, boundary features, or the like of the lesion region. For example, when the feature information (e.g., texture features, boundary features, or the like) of the lesion region has a specific pattern, the size of the sample region may be set to be great; when the feature information (e.g., texture features, boundary features, or the like) of the lesion region has an irregular pattern, the size of the sample region may be set to be small. Alternatively, when the feature information (e.g., texture features, boundary features, or the like) of the lesion region has an irregular pattern because the feature information is limited to a specific part, the size of the sample region may be set to be small with the center at the corresponding portion.

Besides, in extracting the sample region from the lesion region, the computer may extract the sample region 112 by sampling the inner region of the lesion region 110 and may extract the sample regions 111 and 113 by sampling the boundary portion of the lesion region 110.

Also, in extracting the sample region from the lesion region, it is not considered whether a sampling location in the lesion region 110 or a redundant region in the lesion region 110 occurs. In other words, because each sample region is extracted (randomly) from an arbitrary point in the lesion region 110, each sample region may include the inner, boundary, or outer region of the lesion region 110.

Also, in constructing the 'N×N'-sized patch 200, that is, LINA patch data, each extracted sample region 111, 112, or 113 may be positioned in order of the arrangement in the patch 200 or may be positioned at an arbitrary location. That is, finally, the LINA patch data may include 'N×N' sample regions having a predetermined size. Besides, because the LINA patch data is composed of sample regions including all of the inner, border, and outer regions of the lesion region 110, the LINA patch data may be constructed by reflecting both texture information of the lesion and information (e.g., boundary feature information, texture information of boundary regions, or the like) about the boundary of the lesion.

Figure 3:
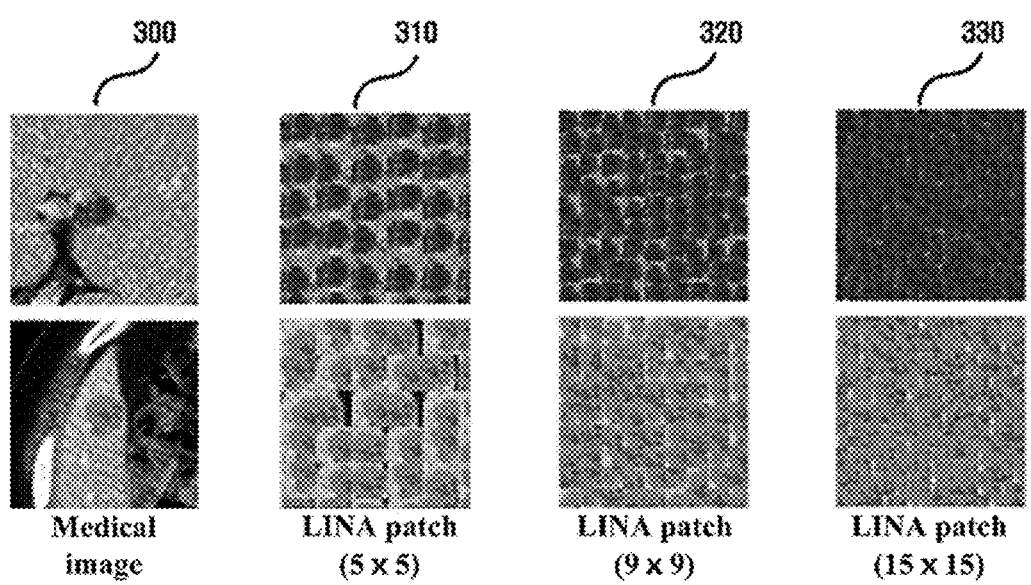
FIG. 3 is a view illustrating examples of LINA patch data generated from a medical image including lesion regions, according to an embodiment of the inventive concept.

FIG. 3 is a view illustrating examples of LINA patch data generated from a medical image including lesion regions, according to an embodiment of the inventive concept.

Referring to FIG. 3, as described above, a computer may generate 'N×N'-sized LINA patch data 310, 320, and 330 by extracting sample regions from a medical image 300 including lesion regions.

For example, the 5×5-sized LINA patch data 310 may include '5×5' sample regions. The 9×9-sized LINA patch data 320 may include '9×9' sample regions. The '15×15'-sized LINA patch data 330 may include '15×15' sample regions.

At this time, the LINA patch data may have the same size as the size of the medical image 300. According to an embodiment, the size of the LINA patch data may be set to a predetermined size.

For example, when the LINA patch data 310, 320, and 330 is determined to be the same size as the size of the medical image 300, the 'N×N'-sized patch data may include 'N×N' sample regions. At this time, as the value of 'N' increases, the size of the sample region in the patch data may decrease. That is, it may be seen that the sample region in the '5×5'-sized LINA patch data 310 has a larger size than the size of the sample region in the '15×15'-sized LINA patch data 330. As described above, the computer may generate the LINA patch by variously setting the size of the sample region (e.g., 5×5, 9×9, 15×15, or the like) depending on the size, shape, and feature of the lesion included in the medical image.

Figure 4:
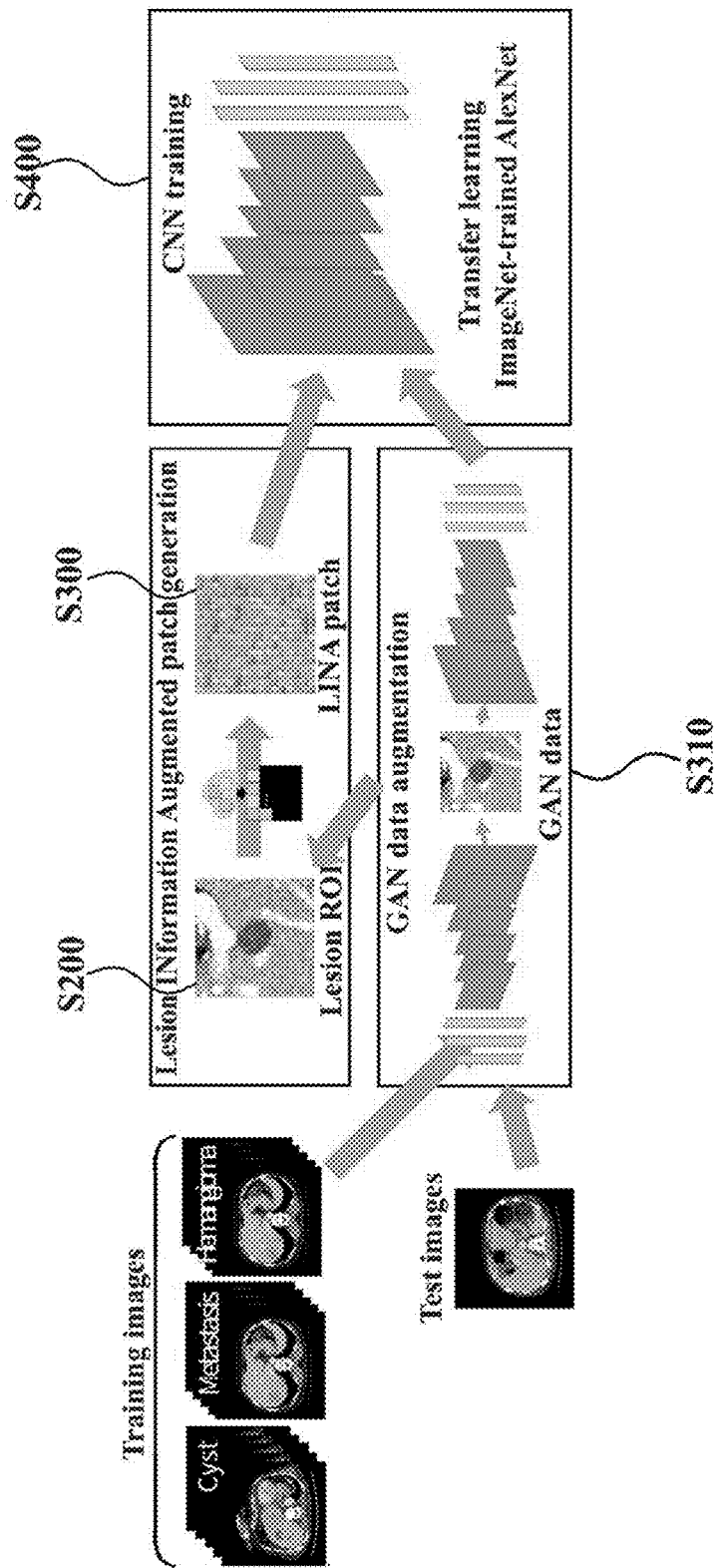
FIG. 4 is an embodiment of applying a learning-based lesion classification method according to an embodiment of the inventive concept and is a view for describing a process of generating LINA patch data and performing learning.

FIG. 4 is an embodiment of applying a learning-based lesion classification method according to an embodiment of the inventive concept and is a view for describing a process of generating LINA patch data and performing learning.

Referring to FIG. 4, in S100, a computer may obtain a medical image including various lesion regions.

In an embodiment, the computer may obtain the medical image including various lesion groups such as cyst, hemangioma, metastasis, or the like.

The computer may extract sample regions from the lesion region in the medical image in S200 and may generate LINA patch data using the extracted sample regions in S300.

In an embodiment, the computer may generate various lesion information by performing scaling or/and rotation on the lesion region in each medical image, based on the medical image for each lesion group. That is, as such, lesion information may be augmented by repeatedly performing scaling or/and rotation on the lesion region in each medical image. Accordingly, the computer may generate the LINA patch data based on the sample regions extracted from lesion regions including the augmented lesion information.

In general, it is not easy to extract image features in the case of microscopic lesions. However, as described above according to an embodiment of the inventive concept, the LINA patch data is generated by augmenting lesion information through scaling or/and rotation on the lesion region included in the medical image, and thus the visual features of the lesion and the visual features of the boundary are augmented even in the case of microscopic lesions. Therefore, it is possible to extract information of the microscopic lesion more effectively and may further improve the learning effect on lesions.

According to an embodiment of the inventive concept, learning data may be reinforced to improve learning efficiency.

In an embodiment, in S310, the computer may perform learning using GAN based on the LINA patch data and may generate synthetic data similar to the LINA patch data. The detailed process thereof will be described with reference to FIG. 5.

Figure 5:
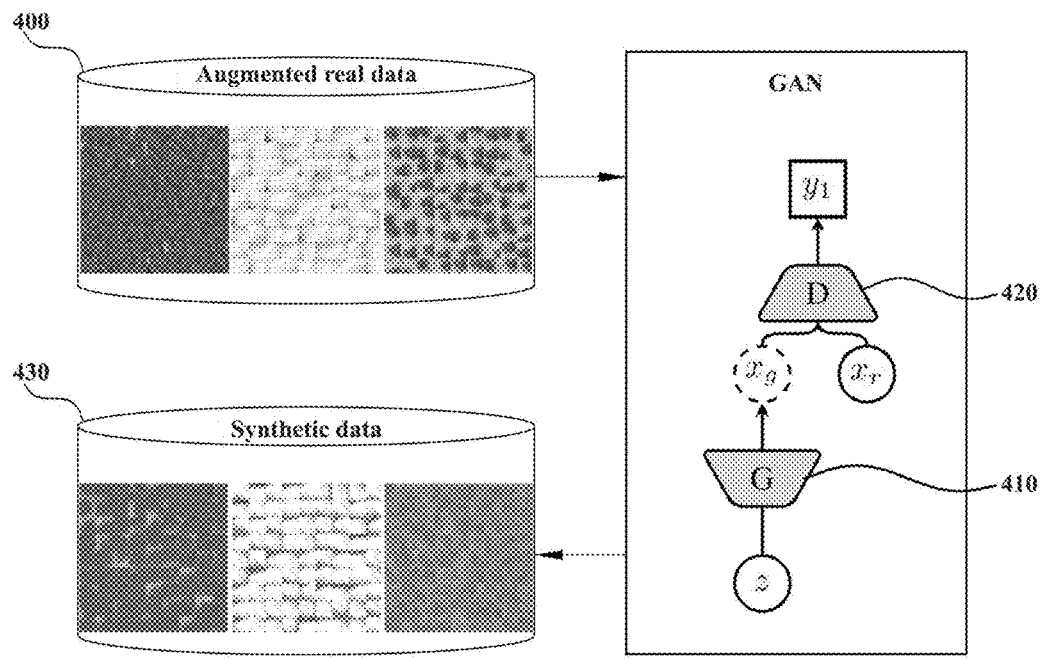
FIG. 5 is a view for describing a method for generating synthetic data using GAN, according to an embodiment of the inventive concept.

FIG. 5 is a view for describing a method for generating synthetic data using GAN, according to an embodiment of the inventive concept.

Referring to FIG. 5, a computer may construct GAN using a generator 410 and a discriminator 420 and may perform learning through the generator 410 and the discriminator 420.

In an embodiment, the generator 410 may perform learning using LINA patch data 400 (i.e., real data) and may generate false data through the learning. In this case, the false data may be false data close to the LINA patch data 400 (i.e., real data). Besides, as described above, the LINA patch data 400 may be LINA patch data including augmented lesion information.

The discriminator 420 performs learning to determine whether the false data generated by the generator 410 is real or false. At this time, the discriminator 420 performs learning to determine whether the false data is genuine, based on the LINA patch data 400 (i.e., real data).

When the determination result indicates that the false data is not genuine, that is, when the generator 410 fails to deceive the discriminator 420, the generator 410 may perform learning again to reduce errors as much as the discriminator 420 is not deceived. The generator 410 may generate the improved false data through re-learning. On the contrary, when the determination result of the discriminator 420 indicates that the false data is real data, that is, when the discriminator 420 is deceived by the generator 410, the discriminator 420 may perform learning again to reduce the error rate (error). Such the process is repeated by the generator 410 and the discriminator 420, thereby generating false data close to reality.

Finally, the computer may generate synthetic data 430 close to the LINA patch data 400 by performing learning using GAN through the generator 410 and the discriminator 420.

At this time, the computer performs learning through GAN independently generated for each lesion group; and as the learning result, the computer may repeatedly generate synthetic data similar to the LINA patch data of each lesion group. For example, the computer may perform learning through GAN on a first lesion group (e.g., a cyst lesion group); as a result, the computer may generate the synthetic data including lesion information of the first lesion group (e.g., a cyst lesion group). In addition, the computer may generate the synthetic data including information about each lesion group by performing learning through GAN on both a hemangioma lesion group and a metastasis lesion group.

According to an embodiment of the inventive concept, because the synthetic data close to real data (LINA patch data) may be additionally generated by performing learning through GAN, it is possible to effectively perform learning even with a small size of a learning data set.

Returning to FIG. 4, in S400, the computer may perform learning based on the LINA patch data generated in S300 and the synthetic data generated in S310 and may classify lesion regions included in the medical image.

In an embodiment, the computer may construct the LINA patch data and/or the synthetic data as the learning data set. Herein, the LINA patch data may refer to LINA patch data including the augmented lesion information.

Moreover, the computer may perform learning using deep learning (e.g., Convolution Neural Network (CNN)) by inputting the learning data set. The computer may classify lesions as the result of learning. For example, the computer may extract at least one of lesion texture information and lesion boundary information from the LINA patch data and/or the synthetic data as a feature map and may classify lesion regions included in the medical image based on the extracted feature map. For example, the computer may classify lesion regions by determining whether the lesion represented by the lesion region in the medical image is cyst, metastasis, hemangioma, or the like. Alternatively, the computer may classify lesion regions by determining whether the lesion represented by the lesion region in the medical image is a malignant tumor or a benign tumor.

An embodiment is exemplified in FIG. 4 as both the LINA patch data and the synthetic data are used as the learning data when the learning for lesion classification is performed, but this is only an example. In another example, the learning for classifying lesions may be performed using only the LINA patch data as the learning data set. In still another example, the learning for classifying lesions may be performed using only the synthetic data as the learning data set.

According to an embodiment of the inventive concept, the classification of the types of lesions included in a medical image may be used to predict the early diagnosis of diseases (e.g., cancer, metastasis, or the like) and may be effectively used for pre-processing tasks such as establishing a surgical plan.

According to an embodiment of the inventive concept, even in the case of microscopic lesions included in the medical image, it is possible to effectively extract the features of the lesion through augmentation of the lesion information. Besides, it is possible to accurately extract the feature of each lesion even among lesions having similar features by constructing LINA patch data, thereby accurately classifying lesions.

According to an embodiment of the inventive concept, even in the case of small medical image data, the learning may be effectively performed to generate a lesion classification model by generating synthetic data close to real data (i.e., LINA patch data) through learning using GAN.

In the meantime, in the related art, learning may be directly performed on the raw medical image; in this process, the misclassification of lesion types such as cyst, metastasis, and the like occurs due to the size bias of a microscopic lesion. Because the brightness feature of the lesion in the raw medical image is not clearly displayed, there was a limitation that the misclassification of lesion types such as hemangioma, metastasis, and the like occurs.

However, according to an embodiment of the inventive concept, because the size bias of the lesion is suppressed through the LINA patch, the misclassification of lesion types such as cyst, metastasis, and the like is reduced, and the learning efficiency for the brightness feature of the lesion is improved. Accordingly, the misclassification of lesion types such as hemangioma, metastasis, and the like is improved.

Furthermore, there is a limitation that learning efficiency decreases due to the small number of data sets upon performing learning in the related art. However, according to an embodiment of the inventive concept, the synthetic data with various lesion patterns may be generated in large quantities by performing learning using GAN. Accordingly, the learning effect is improved upon performing deep learning-based learning.

Figure 6:
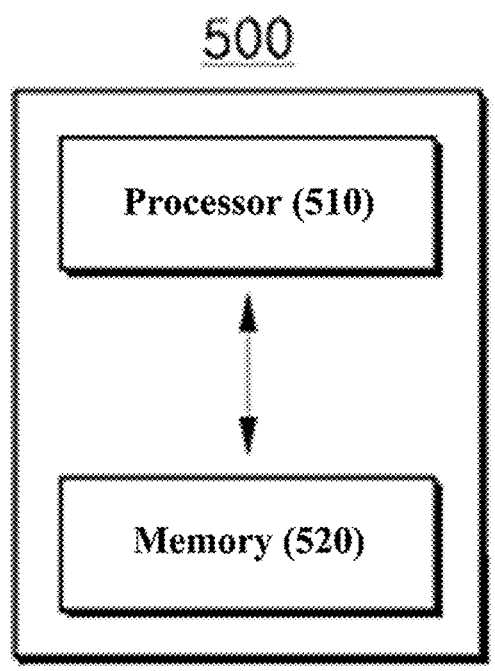
FIG. 6 is a view schematically illustrating a configuration of an apparatus 500 performing a learning-based lesion classification method, according to an embodiment of the inventive concept.

FIG. 6 is a view schematically illustrating a configuration of an apparatus 500 performing a learning-based lesion classification method, according to an embodiment of the inventive concept.

Referring to FIG. 6, the processor 510 may include one or more cores (not illustrated), a graphic processing unit (not illustrated), and/or a connection path (e.g., a bus, or the like) through which a signal is transmitted and received with other components.

According to an embodiment, the processor 510 may perform a learning-based lesion classification method described with reference to FIGS. 1 to 5 by executing one or more instructions stored in a memory 520.

Referring to FIG. 1, the processor 510 may execute one or more instructions stored in the memory 520 and thus may perform obtaining a medical image including lesion regions, extracting at least one sample region from the lesion regions within the medical image, generating LINA patch data based on the at least one sample region, and classifying the lesion regions within the medical image by performing learning based on the LINA patch data.

In the meantime, the processor 510 may further include Random Access Memory (RAM) (not illustrated) and Read-Only Memory (ROM) (not illustrated) that temporarily and/or permanently store a signal (or data) processed inside the processor 510. Furthermore, the processor 510 may be implemented in the form of a system on chip (SoC) including at least one of a graphic processor, RAM, and ROM.

Programs (one or more instructions) for the processing and controlling of the processor 510 may be stored in the memory 520. The programs stored in the memory 520 may be divided into a plurality of modules depending on functions.

The learning-based lesion classification method according to an embodiment of the inventive concept may be implemented by a program (or an application) and may be stored in a medium such that the program is executed in combination with a computer being hardware.

The above-described program may include a code encoded by using a computer language such as C, C++, JAVA, a machine language, or the like, which a processor (CPU) of the computer can read through the device interface of the computer, such that the computer reads the program and performs the methods implemented with the program. The code may include a functional code associated with the function that defines functions necessary to perform the methods, and may include a control code associated with an execution procedure necessary for the processor of the computer to perform the functions in a predetermined procedure. Furthermore, the code may further include additional information necessary for the processor of the computer to perform the functions or a memory reference-related code associated with the location (address) of the internal or external memory of the computer, at which the media needs to be checked. Moreover, when the processor of the computer needs to communicate with any other remote computer or any other remote server to perform the functions, the code may further include a communication-related code associated with how to communicate with any other remote computer or server using the communication module of the computer, what information or media should be transmitted or received during communication, or the like.

The stored media may mean the media that does not store data for a short period such as a register, a cache, a memory, or the like but semi-permanently stores to be read by the device. Specifically, for example, the stored media include, but are not limited to, ROM, RAM, CD-ROM, magnetic tape, floppy disk, optical data storage device, and the like. That is, the program may be stored in various recording media on various servers that the computer can access, or various recording media on the computer of the user. In addition, the media may be distributed to a computer system connected to a network, and a computer-readable code may be stored in a distributed manner.

The steps of a method or algorithm described in connection with the embodiments of the inventive concept may be embodied directly in hardware, in a software module executed by hardware, or in a combination thereof. The software module may reside on a Random Access Memory (RAM), a Read Only Memory (ROM), an Erasable Programmable ROM (EPROM), an Electrically Erasable Programmable ROM (EEPROM), a Flash memory, a hard disk, a removable disk, a CD-ROM, or a computer-readable recording medium in any form known in the art to which the inventive concept pertains.

Although embodiments of the inventive concept have been described herein with reference to accompanying drawings, it should be understood by those skilled in the art that the inventive concept may be embodied in other specific forms without departing from the spirit or essential features thereof. Therefore, the above-described embodiments are exemplary in all aspects, and should be construed not to be restrictive.

According to an embodiment of the inventive concept, the classification of the types of lesions included in a medical image may be used to predict the early diagnosis of diseases (e.g., cancer, metastasis, or the like) and may be effectively used for pre-processing tasks such as establishing a surgical plan.

According to an embodiment of the inventive concept, even in the case of microscopic lesions included in the medical image, it is possible to effectively extract the features of the lesion through augmentation of the lesion information. Besides, it is possible to accurately extract the feature of each lesion even among lesions having similar features by constructing LINA patch data, thereby accurately classifying lesions.

According to an embodiment of the inventive concept, even in the case of small medical image data, the learning may be effectively performed to generate a lesion classification model by generating synthetic data close to real data (i.e., LINA patch data) through learning using GAN.

The effects of the present inventive concept are not limited to the aforementioned effects, and other effects not mentioned herein will be clearly understood from the following description by those skilled in the art to which the inventive concept pertains.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A learning-based lesion classification method performed by a computer, the method comprising:
    obtaining a computerized tomography (CT) medical image including a lesion region;
    augmenting boundary information and texture information of a lesion included in the lesion region, and extracting a plurality of sample regions based on the augmented information;
    repeatedly positioning the plurality of sample regions in a patch having a first predetermined size that is greater than a size of a respective sample region of the plurality of sample regions, to generate lesion information augmented patch (LINA patch) data; and
    classifying lesions included in the lesion region within the medical image by performing learning based on the augmented information included in the LINA patch data.

2. The method of claim 1, wherein the extracting the plurality of sample regions comprises:
    selecting a plurality of arbitrary points from the lesion region within the medical image; and
    extracting the respective sample region of the plurality of sample regions with a center at a respective arbitrary point of the plurality of arbitrary point.

3. The method of claim 1, wherein the first predetermined size is an 'N×N' size.

4. The method of claim 3,
    wherein the augmenting comprises:
    performing at least one of scaling and rotation on the lesion region within the medical image.

5. The method of claim 3, further comprises:
    learning the LINA patch data, using generative adversarial network (GAN); and
    generating synthetic data for the LINA patch data, through the learning using the GAN.

6. The method of claim 5, wherein the classifying comprises:
    performing the learning using Convolutional Neural Network (CNN) based on at least one of the LINA patch data and the synthetic data; and
    classifying the lesions included in the lesion region through the learning using the CNN.

7. The method of claim 6, wherein the performing of the learning using CNN includes:
    performing the learning based on at least one of the texture information and the boundary information.

8. The method of claim 3, wherein the respective sample region is a region formed of a square of a second predetermined size, and the size of the respective sample region is determined depending on a size or shape of the lesion region, and
    wherein the LINA patch data includes 'N×N' sample regions formed of the square of the second predetermined size.

9. A non-transitory computer readable recording medium, coupled to a hardware computer device, and storing a computer program configured to perform the method of claim 1.

10. An apparatus comprising:
    a memory configured to store one or more instructions; and
    a processor configured to execute the one or more instructions stored in the memory, wherein the one or more instructions, when executed by the processor, cause the processor to:

obtain a computerized tomography (CT) medical image including a lesion region;

augment boundary information and texture information of a lesion included in the lesion region, and extract a plurality of sample regions based on the augmented information;

repeatedly position the plurality of sample regions in a patch having a first predetermined size that is greater than a size of a respective sample region of the plurality of sample regions, to generate LINA patch data; and classify lesions included in the lesion region within the medical image by performing learning based on the augmented information included in the LINA patch data.

* * * * *